(12) United States Patent
Xie et al.

(10) Patent No.: US 11,154,689 B2
(45) Date of Patent: Oct. 26, 2021

(54) VASCULAR INTERVENTIONAL INSTRUMENT CONTROL DEVICE WITH DOUBLE GUIDE WIRES OR BALLOONS

(71) Applicant: INSTITUTE OF AUTOMATION, CHINESE ACADEMY OF SCIENCES, Beijing (CN)

(72) Inventors: Xiaoliang Xie, Beijing (CN); Zengguang Hou, Beijing (CN); Lingwu Meng, Beijing (CN); Zhenqiu Feng, Beijing (CN); Xiaohu Zhou, Beijing (CN); Shiqi Liu, Beijing (CN)

(73) Assignee: INSTITUTE OF AUTOMATION, CHINESE ACADEMY OF SCIENCES, Beijing (CN)

(*) Notice: Subject to any disclaimer, the term of this patent is extended or adjusted under 35 U.S.C. 154(b) by 0 days.

(21) Appl. No.: 17/044,513

(22) PCT Filed: Nov. 12, 2019

(86) PCT No.: PCT/CN2019/117493
§ 371 (c)(1),
(2) Date: Oct. 1, 2020

(87) PCT Pub. No.: WO2021/051552
PCT Pub. Date: Mar. 25, 2021

(65) Prior Publication Data
US 2021/0268231 A1     Sep. 2, 2021

(30) Foreign Application Priority Data

Sep. 19, 2019 (CN) .......................... 201910887426.6

(51) Int. Cl.
*A61M 25/01*     (2006.01)
*A61M 25/09*     (2006.01)
(Continued)

(52) U.S. Cl.
CPC ......... *A61M 25/0113* (2013.01); *A61B 34/30* (2016.02); *A61M 25/09041* (2013.01); *A61M 25/1011* (2013.01); *A61B 2034/301* (2016.02)

(58) Field of Classification Search
CPC ........ A61M 25/0113; A61M 25/09041; A61M 25/1011; A61B 34/30; A61B 2034/301
See application file for complete search history.

(56) References Cited

U.S. PATENT DOCUMENTS 7,998,020 B2    8/2011    Kidd et al.
2007/0060879 A1* 3/2007   Weitzner ......... A61M 25/10184
                                                      604/95.04

(Continued)

FOREIGN PATENT DOCUMENTS

CN    101247847 A    8/2008
CN    103006327 A    4/2013

(Continued)

*Primary Examiner* — Nathan R Price
*Assistant Examiner* — Justin L Zamory
(74) *Attorney, Agent, or Firm* — Bayramoglu Law Offices LLC

(57) ABSTRACT

A vascular interventional instrument control device capable of operating double guide wires or balloons, includes a main finger assembly, a first sub-finger assembly, a second sub-finger assembly, a driving assembly and a clamping assembly, wherein the main finger assembly, the sub-finger assembly, the driving assembly and the clamping assembly are separately installed to the body structural member and separately connected to the controller through a communication link, one of the operated double guide wires or balloons is clamped by the main finger assembly and the first sub-finger assembly, and the other is clamped by the main finger assembly and the second sub-finger assembly; and the operated double guide wires or double balloons can be separately moved axially or rotated about its own axial direction.

10 Claims, 5 Drawing Sheets

(51) Int. Cl.
*A61B 34/30* (2016.01)
*A61M 25/10* (2013.01)

(56) References Cited

U.S. PATENT DOCUMENTS

| | | | | |
|---|---|---|---|---|
| 2011/0264038 A1 * | 10/2011 | Fujimoto | ........... | A61M 25/0113 604/95.01 |
| 2016/0354582 A1 | 12/2016 | Yu et al. | | |

FOREIGN PATENT DOCUMENTS

| | | | |
|---|---|---|---|
| CN | 103083784 | A | 5/2013 |
| CN | 103157170 | A | 6/2013 |
| CN | 106880380 | A | 6/2017 |
| CN | 107349514 | A | 11/2017 |
| CN | 108309370 | A | 7/2018 |
| CN | 109821137 | A | 5/2019 |
| CN | 110200700 | A | 9/2019 |
| EP | 0970714 | A2 | 1/2000 |
| WO | 9956920 | A1 | 11/1999 |
| WO | 2018017641 | A3 | 5/2018 |
| WO | 2019133438 | A1 | 7/2019 |

* cited by examiner

VASCULAR INTERVENTIONAL INSTRUMENT CONTROL DEVICE WITH DOUBLE GUIDE WIRES OR BALLOONS

CROSS REFERENCE TO THE RELATED APPLICATIONS

This application is the national phase entry of International Application No. PCT/CN2019/117493, filed on Nov. 12, 2019, which is based upon and claims priority to Chinese Patent Application No. 201910887426.6, filed on Sep. 19, 2019, the entire contents of which are incorporated herein by reference.

TECHNICAL FIELD

The present invention relates to the technical field of surgical robots, and in particular to a vascular interventional instrument control device with double guide wires or balloons.

BACKGROUND

Bifurcation lesions refer to stenosis of blood vessels caused by plaques, blockages, etc. in the blood vessels, and exist in multiple locations within the blood vessels, especially at the bifurcation of the blood vessels. At present, coronary bifurcation lesions account for a large proportion of percutaneous coronary intervention (PCI) surgery. Due to the complexity of the lesion location, bifurcation angle and type, the technical operation is difficult and the surgical time is long, which has become a problem in the PCI surgery. A surgical robot is urgently needed to solve this problem. For the bifurcation lesions, the double-stent technology is mainly used clinically. The key of this technology is to ensure that main-branch vessels and side-branch vessels are unobstructed at the same time, that is, main-branch and side-branch stents need to be in place at the same time. The existing vascular minimally-invasive interventional surgery robot can only push a single guide wire at a time, so that the surgical time for patients with bifurcation lesions is long, the exposure time under radiation environment is long, and the labor intensity of doctors is large. Moreover, since the existing PCI surgical robot can only perform an operation of pushing a single guide wire or catheter at a time, the surgical efficiency is low, the workload is large, and the treatment time is long, which cannot meet the needs of the surgery.

SUMMARY

In order to solve the above-mentioned problems in the prior art, namely, the surgical robots can only realize the operation control of a single guide wire or balloon catheter, resulting in low surgical efficiency, large workload, long treatment time, and large labor intensity of doctors, the present invention provides a vascular interventional instrument control device capable of operating double guide wires or balloons. A user can use a surgical robot to push two guide wires one after another to reach different lesion locations, respectively, and then push and release balloons and stents, realizing a surgical treatment, greatly improving the work efficiency, and better handling the bifurcation lesions. The vascular interventional instrument control device with double guide wires or balloons of the present invention includes a body structural member, a main finger assembly, a sub-finger assembly, a driving assembly, a clamping assembly and a controller, the main finger assembly, the sub-finger assembly, the driving assembly and the clamping assembly being separately installed to the body structural member and being separately connected to the controller through a communication link, wherein the sub-finger assembly includes a first sub-finger assembly and a second sub-finger assembly, and the clamping assembly includes a first clamping assembly for clamping a first guide wire or balloon, and a second clamping assembly for clamping a second guide wire or balloon;

the main finger assembly includes a main roller, the first sub-finger assembly includes a first sub-roller, and the second sub-finger assembly includes a second sub-roller; the main roller, the first sub-roller, and the second sub-roller have axes disposed in parallel; and the first sub-roller and the second sub-roller are mirror-symmetrical with respect to the axis of the main roller;

the first sub-finger assembly is provided with a first wheelbase adjustment device, an axial distance between the first sub-roller and the main roller can be adjusted by the first wheelbase adjustment device, so as to clamp or release the first guide wire or balloon; and the second sub-finger assembly is provided with a second wheelbase adjustment device, an axial distance between the second sub-roller and the main roller can be adjusted by the second wheelbase adjustment device, so as to clamp or release the second guide wire or balloon;

when the first guide wire or balloon is clamped by the main roller and the first sub-roller, the first guide wire or balloon can be displaced along its own axial direction by means of axial rotation of the main roller; the main finger assembly, and the first sub-finger assembly can be separately moved axially by means of driving of the driving assembly, for twisting the clamped first guide wire or balloon to rotate about its own axial direction; and when the second guide wire or balloon is clamped by the main roller and the second sub-roller, the second guide wire or balloon can be displaced along its own axial direction by means of active rotation of the main roller; the main finger assembly, and the second sub-finger assembly can be separately moved axially by means of the driving of the driving assembly, for twisting the clamped second guide wire or balloon to rotate about its own axial direction.

Preferably, the first sub-roller is driven close to or away from the main roller by the wheelbase adjustment device, so that the first guide wire or balloon disposed between the first sub-roller and the main roller is clamped or released;

the second sub-roller is driven close to or away from the main roller by the wheelbase adjustment device, so that the second guide wire or balloon disposed between the second sub-roller and the main roller is clamped or released; and at the same time, the two guide wires or balloons being operated have different clamping states, and movement of the main roller does not interfere with the released guide wires or balloons.

Preferably, the body structural member includes a top plate and a web plate perpendicular to the top plate, and at least three through holes are provided on the web plate; and the body structural member is divided into a driving part and an executing part by the web plate, the main finger assembly, the first sub-finger assembly, and the second sub-finger assembly are separately disposed in the executing part, and the driving assembly and the clamping assembly are disposed in the driving part.

Preferably, the main finger assembly includes a main finger power device, a main finger transmission mechanism and a main finger guide rail mechanism, the main finger transmission mechanism includes a coupling, the main finger power device includes a propelling motor, an output shaft of the propelling motor is coaxially connected to the main roller through the coupling, and the main roller is driven by the propelling motor to rotate axially about the output shaft of the propelling motor;

the main finger guide rail mechanism includes a main finger guide rail and a main finger slider, the main finger guide rail is vertically fixed to the web plate, and the main roller is slidingly disposed to the main finger guide rail through the main finger slider to form a linearly moving pair; and the main roller is driven by the driving assembly drives to move up and down along a vertical direction through the linearly moving pair.

Preferably, the first sub-finger assembly and the second sub-finger assembly have the same structure, and both comprise a wheelbase adjustment device and a sub-finger guide rail mechanism, and the wheelbase adjustment device includes a sub-finger power device and a sub-finger transmission mechanism; and the sub-finger transmission mechanism is a gear transmission, the sub-finger power device includes a clamping motor, and rotational motions of output shafts of the two clamping motors drive the first sub-roller and the second sub-roller to move toward or away from the main roller by means of gear transmission, respectively;

the sub-finger guide rail mechanism includes a sub-finger guide rail and a sub-finger slider, the two sub-finger guide rails are symmetrically arranged on both sides of the main finger guide rail, and both are fixed vertically to the web plate, the first sub-roller and the second sub-roller are slidingly disposed to the sub-finger guide rail through the sub-finger slider, respectively, to form a first linearly moving pair and a second linearly moving pair; and the driving assembly drives the first sub-roller and the second sub-roller to move up and down along a vertical direction through the first linearly moving pair and the second linearly moving pair, respectively.

Preferably, the driving assembly includes a first power device, a main finger assembly transmission member, a first sub-finger assembly transmission member, and a second sub-finger assembly transmission member; the main finger assembly transmission member is driven by the first power device to perform a repetitive displacement motion with the first sub-finger assembly transmission member and/or the second sub-finger assembly transmission member, so that the main finger assembly and the first sub-finger assembly and/or the second sub-finger assembly form an axial displacement to twist the clamped guide wire or balloon being operated to rotate.

Preferably, the driving assembly further includes a thrust plate, the main finger assembly transmission member, the first sub-finger assembly transmission member and the second sub-finger assembly transmission member have the same structure, and each comprise a gear, a screw, and a screw base matched with the screw, the screw is disposed below the gear through the thrust plate and is coaxially connected to the gear, the screw base is sleeved to the screw, and the three screw bases are connected to the main roller assembly, the first sub-roller assembly, and the second sub-roller assembly, respectively; and the first power device including a twisting motor; a rotational motion of an output shaft of the twisting motor is converted into a repetitive displacement motion through the gear and the screw and is transferred to the main roller assembly, the first sub-roller assembly and the second sub-roller assembly.

Preferably, the first clamping assembly and the second clamping assembly have the same structure, and each includes a second power device, and a clamping transmission assembly, and the clamping transmission assembly includes a fixed part and a movable part, and the movable part is driven by the second power device to perform the repetitive displacement motion, so that the fixed part and the movable part form a moving pair for clamping or releasing the operated guide wire or balloon.

Preferably, the fixed part includes a clamping guide rail and a fixed clamping end, the movable part includes a clamping slider and a movable clamping end, the clamping slider cooperates with the clamping guide rail, and the clamping slider is connected to the movable clamping end, the fixed clamping end is symmetrically disposed with the movable clamping end, and the fixed clamping end and the movable clamping end are each provided with a guide groove at an end close to each other; and the second power device includes a clamping motor, a clamping gear is provided on an output shaft of the clamping motor, the clamping slider is provided with a rack meshed with the clamping gear at an end close to the clamping gear, and the second power device drives the clamping gear, so that the slider drives the movable clamping end to displace.

Preferably, the main roller, the first sub-roller, and the second sub-roller each comprise a roller and a rubber jacket, and the rubber jacket is sleeved on the roller through an interference fit.

The advantages of the present invention are as follows.

In the present invention, the two sub-rollers approximate to and separate from the main roller through the wheelbase adjusting devices in the two sub-finger assemblies, respectively, to clamp or release the two guide wires or balloons, and the relative movement between the main roller and the sub-roller advances and rotates the clamped guide wire or balloon, thereby realizing separate control of the two guide wires or balloons. The two guide wires or balloons are separately powered by the propelling motor in the main finger assembly to realize the forward/backward movement; the relative movement of each guide wire or balloon in the axial direction is powered by the twisting motor in the driving assembly to realize the combined movement between the main roller and the sub-roller, thereby realizing the forward and reverse rotational motions of the guide wire or balloon catheter; it is powered by the clamping motor in the sub-finger assembly to realize the distance adjustment and tensioning work between the main roller and the sub-roller; and after the guide wire or balloon reaches the lesion location, the guide wire or balloon is clamped by the clamping assembly to prevent the guide wire or balloon from wandering. Through the above actions, realizing the operation of pushing the double guide wires can save the operation step of the doctor to replace the surgical instrument, reduce the doctor's operation burden, improve the surgical efficiency, reduce the surgical cost, reduce the patient's pain, enhance the patient's comfort during surgery, and ensure that the surgery is carried out smoothly, which has strong clinical applicability and wide application prospects.

BRIEF DESCRIPTION OF THE DRAWINGS

By reading the detailed description of the non-limiting embodiments made with reference to the following drawings, other features, objectives, and advantages of the present application will become more apparent.

DETAILED DESCRIPTION OF THE INVENTION

Figure 1:
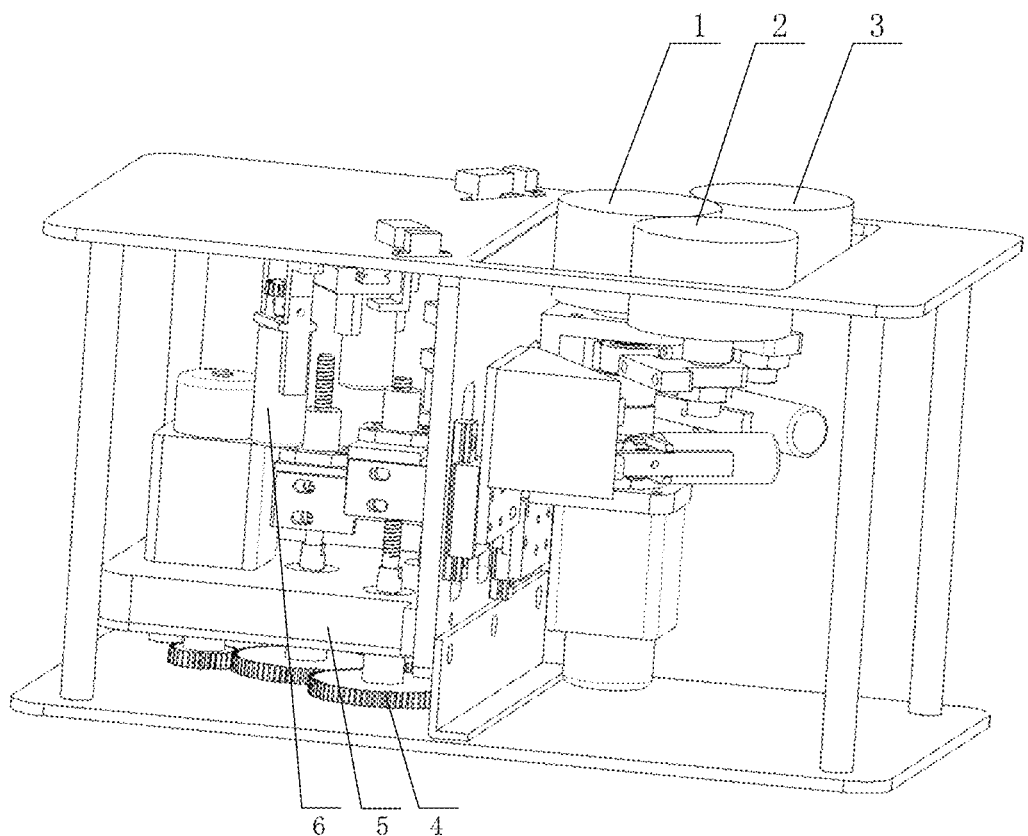
FIG. 1 is a schematic structural diagram of a vascular interventional instrument control device with double guide wires or balloons according to an embodiment of the present invention.

In order to make the embodiments, technical solutions and advantages of the present invention more obvious, the technical solutions of the present invention will be clearly and completely described below in conjunction with the drawings. Obviously, the described embodiments are a part of the embodiments of the present invention, but not all the embodiments. It should be understood by those skilled in the art that these embodiments are only used to explain the technical principles of the present invention, and are not intended to limit the protection scope of the present invention.

A vascular interventional instrument control device with double guide wires or balloons of the present invention includes a body structural member, a main finger assembly, a sub-finger assembly, a driving assembly, a clamping assembly, a controller, the main finger assembly, the sub-finger assembly, the driving assembly and the clamping assembly being each installed to the body structural member and being separately connected to the controller through a communication link, wherein the sub-finger assembly includes a first sub-finger assembly and a second sub-finger assembly, and the clamping assembly includes a first clamping assembly for clamping a first guide wire or balloon, and a second clamping assembly for clamping a second guide wire or balloon;

the main finger assembly includes a main roller, the first sub-finger assembly includes a first sub-roller, and the second sub-finger assembly includes a second sub-roller; the main roller, the first sub-roller, and the second sub-roller have axes disposed in parallel; and the first sub-roller and the second sub-roller are mirror-symmetrical with respect to the axis of the main roller;

the first sub-finger assembly is provided with a first wheelbase adjustment device, an axial distance between the first sub-roller and the main roller can be adjusted by the first wheelbase adjustment device, so as to clamp or release the first guide wire or balloon; and the second sub-finger assembly is provided with a second wheelbase adjustment device, an axial distance between the second sub-roller and the main roller can be adjusted by the second wheelbase adjustment device, so as to clamp or release the second guide wire or balloon;

when the first guide wire or balloon is clamped by the main roller and the first sub-roller, the first guide wire or balloon can be displaced along its own axial direction by means of axial rotation of the main roller; the main finger assembly, and the first sub-finger assembly can be separately moved axially by means of driving of the driving assembly, for twisting the clamped first guide wire or balloon to rotate about its own axial direction; and when the second guide wire or balloon is clamped by the main roller and the second sub-roller, the second guide wire or balloon can be displaced along its own axial direction by means of axial rotation of the main roller; and the main finger assembly, and the second sub-finger assembly can be separately moved axially by means of driving of the driving assembly, for twisting the clamped second guide wire or balloon to rotate about its own axial direction.

In some embodiments of the present invention, the first sub-roller is driven close to or away from the main roller by the wheelbase adjustment device, so that the first guide wire or balloon disposed between the first sub-roller and the main roller is clamped or released;

the second sub-roller is driven close to or away from the main roller by the wheelbase adjustment device, so that the second guide wire or balloon disposed between the second sub-roller and the main roller is clamped or released; and at the same time, the two guide wires or balloons being operated have different clamping states, and movement of the main roller does not interfere with the released guide wires or balloons.

In order to more clearly explain the vascular interventional instrument control device with double guide wires or balloons of the present invention, a preferred embodiment of the present invention will be described in detail with reference to the drawings.

The sub-finger assembly includes a first sub-finger assembly and a second sub-finger assembly, and the clamping assembly includes a first clamping assembly for clamping a first guide wire or balloon, and a second clamping assembly for clamping a second guide wire or balloon.

FIG. 1 is a schematic view of the overall structure of the embodiment. Referring to FIG. 1, the vascular interventional instrument control device capable of operating double guide wires or balloons of the present invention includes the main finger assembly 1, the sub-finger assembly, the driving assembly 4, and the body structural member 5 and the clamping assembly 6. The main finger assembly 1, the sub-finger assembly, the driving assembly 4, the body structural member 5 and the clamping assembly 6 are separately installed on the body structural member 5, and are separately connected to the controller through a communication link, wherein the sub-finger assembly includes the first sub-finger assembly 2 and the second sub-finger assembly 3; and the clamping assembly 6 includes a first clamping assembly for clamping a first guide wire or balloon, and a second clamping assembly for clamping a second guide wire or balloon. The controller is not shown in the figure. The controller may be a central control unit, a wire handle control end, a processor, a display or the like. The specific structure and control mode of the controller are not limited, and are not within the scope of the description of the present invention, and those skilled in the art can use well-known techniques as needed.

A vascular interventional instrument control device capable of operating double guide wires or balloons provided in an embodiment of the present invention can control the double guide wires or catheters to complete the advancement, rotation, and simultaneous movements of advancement and rotation in a blood vessel to better deal with the problem of bifurcation lesions. The propelling motor in the main finger assembly is connected to the main roller through a coupling and a roller support shaft, and drives the main roller to rotate, realizing the guide wire pushing operation using friction by means of cooperation with the first sub-finger assembly 2 and the second sub-finger assembly 3. The main finger assembly is connected to the driving assembly. The twisting motor in the driving assembly converts a rotational motion into a linear motion through the screw, and the relative movement of the main roller and the two sub-rollers is realized through the guide rail pair, thus achieving the purpose of rotating and twisting the two guide wires. It should be noted that the surfaces of the sub-roller and the main roller are provided with rubber jackets, which play a function of increasing the friction between the guide wire or catheter and the rollers. Since the outer wall of the guide wire or catheter is in contact with the main finger assembly 1 and the first sub-finger assembly 2 or the second sub-finger assembly 3, care must be taken to prevent the outer surface coating of the guide wire or balloon from being damaged. The vascular interventional instrument control device with double guide wires or balloons of the present invention can control double guide wires or double balloons or double catheters, which may be replaced by medical tools as long as they conform to the installation dimensions and the driving principles of the present invention. They will not be exhaustively listed here. It should be noted that the title of the present invention is not intended to limit the use of the present invention.

Figure 3:
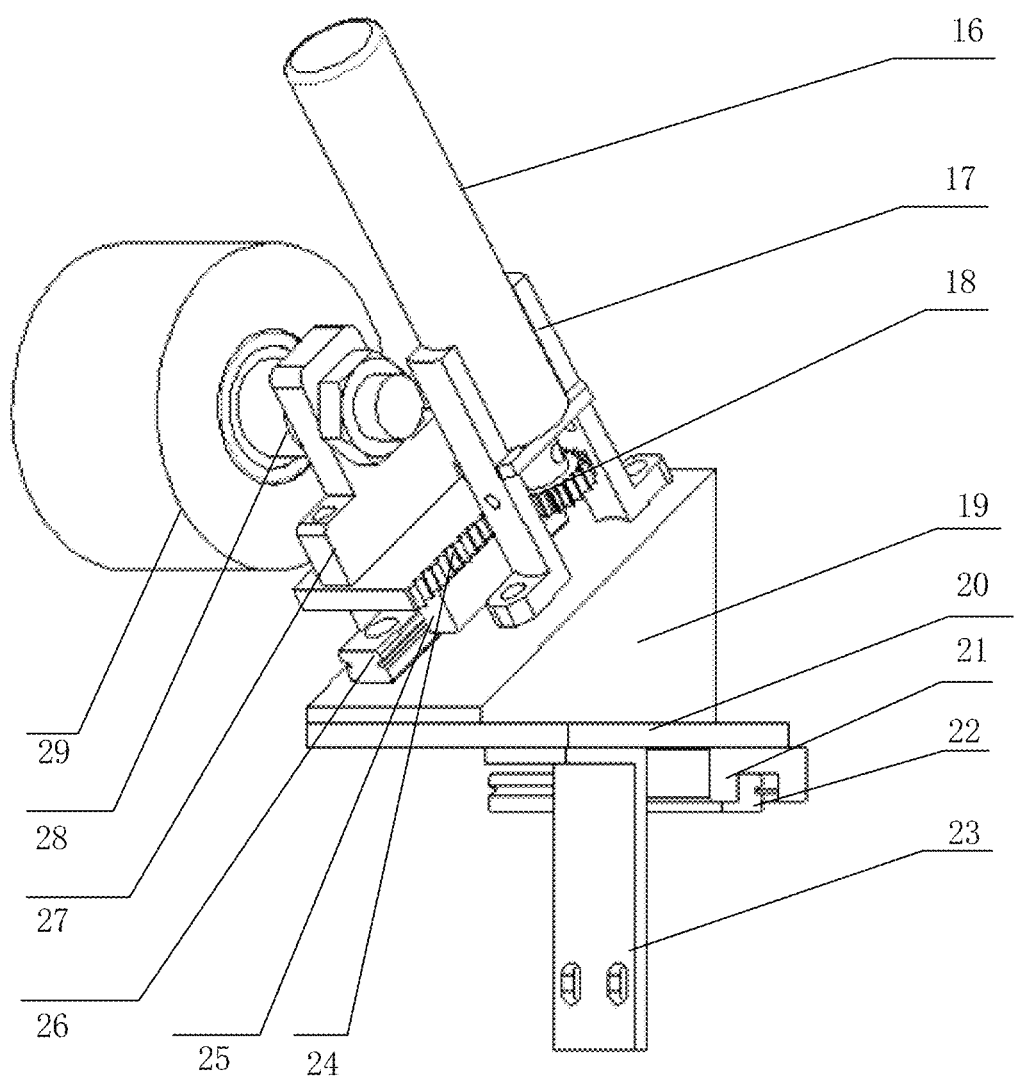
FIG. 3 is a schematic structural diagram of a first sub-finger assembly in an embodiment of the present invention.

The main finger assembly 1 includes the main roller 11. The first sub-finger assembly 2 includes the first sub-roller 29, and the second sub-finger assembly includes a second sub-roller. The main roller 11, the first sub-roller 29, and the second sub-roller have axes disposed in parallel. The first sub-roller 29 and the second sub-roller are disposed to be mirror-symmetrical with respect to the axis of the main roller 11, and the two sub-rollers are disposed to fit the main roller 11 in a normal state. The axis here refers to a perpendicular line that passes through a geometric center of the roller and is perpendicular to a plane where the roller is located, or is understood as a center line of the roller. In the embodiment, the main roller 11, the first sub-roller 29, and the second sub-roller each comprise a roller and a rubber jacket, and the rubber jacket is sleeved on the roller through an interference fit. In the present invention, the first sub-finger assembly and the second sub-finger assembly in the sub-finger assembly have substantially the same structure and motion relationship. Thus, the embodiment is illustrated with the first sub-finger assembly as an example. FIG. 3 is a structural diagram of the first sub-finger assembly 2, and the structure of the second sub-finger assembly 3 is similarly referred to FIG. 3.

Further, the first sub-finger assembly 2 is provided with a first wheelbase adjustment device, by which an axial distance between the first sub-roller 29 and the main roller 11 can be adjusted to clamp or release the first guide wire or balloon. The second sub-finger assembly 3 is provided with a second wheelbase adjustment device, by which an axis distance between the second sub-roller and the main roller 11 can be adjusted to clamp or release the second guide wire or balloon. When the first sub-roller 29 is driven by the first wheelbase adjustment device to be in close contact with the main roller 11, the first guide wire or balloon disposed between the first sub-roller 29 and the main roller 11 can be clamped. Similarly, when the second sub-roller is driven by the second wheelbase adjustment device to be in close contact with the main roller 11, the second guide wire or balloon disposed between the second sub-roller and the main roller 11 can be clamped.

The first guide wire or balloon is clamped by the first sub-roller 29 and the main roller 11, and when the first guide wire or balloon is clamped, it can be displaced along its own axial direction by the active rotation of the main roller 11. The main finger assembly 1 and the first sub-finger assembly 2 can be separately driven by the driving assembly 4 to move axially, and the main finger assembly 1 and the first sub-finger assembly 2 can twist the clamped first guide wire or balloon by combined movement to perform a forward or reverse rotational motion about its own axial direction. Similarly, the second guide wire or balloon is clamped by the main roller 11 and the second sub-roller, and when the second guide wire or balloon is clamped, it can be displaced along its own axial direction by the active rotation of the main roller 11. The main finger assembly 1 and the second sub-finger assembly 3 can be driven by the driving assembly 4 to move axially for twisting the clamped second guide wire or balloon to rotate about its own axial direction. The term "own axial direction" in the description of this paragraph refers to the own longitudinal direction of the guide wire or catheter or balloon's is used as an axis.

Specifically, the first sub-roller 29 of the present invention can be driven close to or away from the main roller 11 by the first wheelbase adjustment device, so that the first guide wire or balloon disposed between the first sub-roller and the main roller is clamped or released. When the first sub-roller 29 is close to the main roller 11, the first guide wire or balloon is clamped. When the first sub-roller 29 is away from the main roller 11, the first guide wire or balloon is released. When the first guide wire or balloon is released, the movement of the main roller 11 cannot interfere with the first guide wire or balloon, that is, when the main roller 11 rolls, the first guide wire or balloon will not move, and when the main roller 11 is displaced, the first guide wire or balloon will not rotate. Similarly, the second sub-roller is driven close to or away from the main roller 11 by the second wheelbase adjustment device, so that the second guide wire or balloon disposed between the second sub-roller and the main roller 11 can also be clamped or released. Correspondingly, the structure of the vascular interventional instrument control device with double guide wires of the present invention can realize simultaneous clamping, simultaneous release, simultaneous rotation and simultaneous displacement of the two guide wires or balloons. However, since the present invention is a surgical robot, it is set to match the design of vascular surgery, and the two catheters do not need to rotate or move at the same time during surgery. Thus, when the present invention is applied, the two guide wires or balloons being operated have different clamping states at the same time, that is, when the first guide wire or balloon is clamped, the second guide wire or balloon is released, and when the first guide wire or balloon is released, the second guide wire or balloon is clamped.

Figure 5:
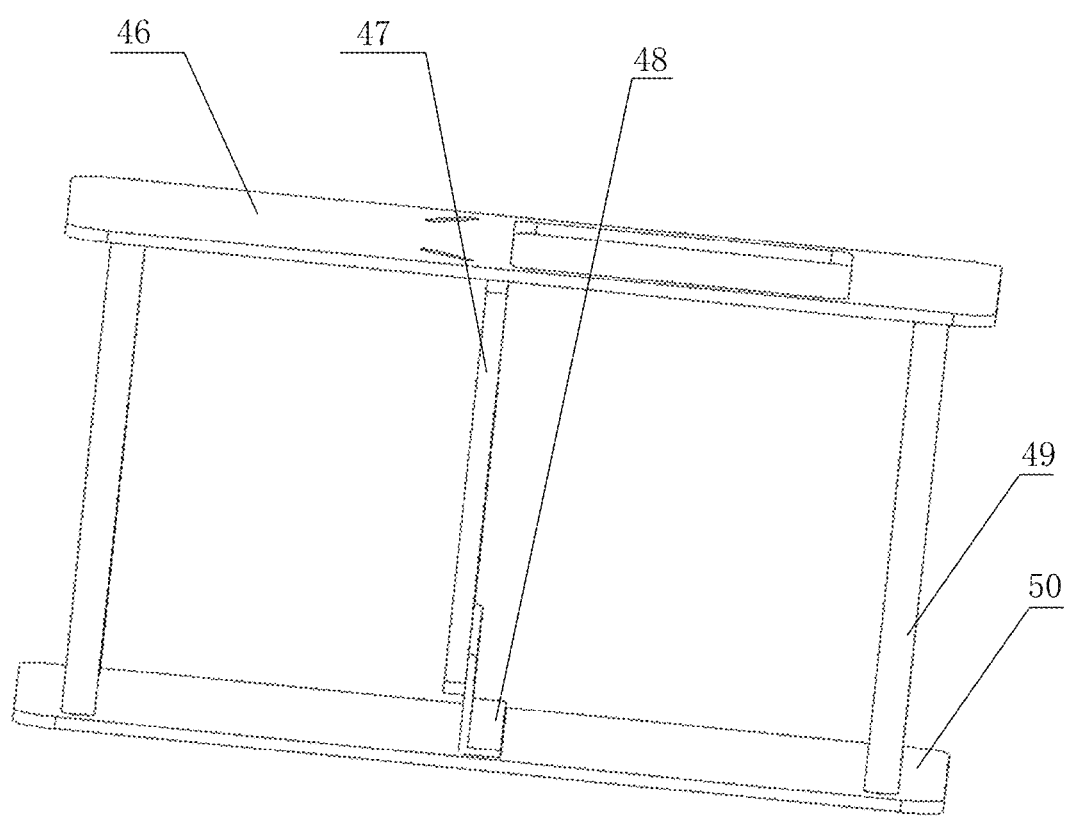
FIG. 5 is a schematic structural diagram of a body structural member in an embodiment of the present invention.

Referring to FIG. 5, considering the protection and support for each assembly, in this embodiment, the body structural member is provided as a box structure. As shown in FIG. 5, the body structural member of this embodiment includes the top plate 46, the web plate 47, the bottom plate connecting frame 48, the column 49, and the bottom plate 50. The web plate 47 of the present invention is disposed below the top plate 46 and is perpendicular to the top plate 46. The web plate 47 divides the body structural member 5 into a driving part and an executing part. The main finger assembly 1, the first sub-finger assembly 2, and the second sub-finger assembly 3 are separately installed in the executing part, and the driving assembly 4 and the clamping assembly 6 are each disposed in the driving part. The web plate 47 is used to install the main finger assembly 1, the first sub-finger assembly 2, the second sub-finger assembly 3, and the driving assembly 4. Preferably, three through holes are provided on the web plate 47, which are used for the axial movement of the main finger assembly 1, the first sub-finger assembly 2 and the second sub-finger assembly 3, respectively. In order to avoid interference, they will not touch walls of the through holes during moving. The bottom plate 50 is used to support the entire device. The four columns are evenly distributed between the top plate and the bottom plate for support. A clamping assembly 6 is provided on the top plate 46, and the bottom plate connecting frame 49 is connected to the bottom plate 50 and the web plate 47 by bolts. The body structural member in this embodiment is only an illustration, and those skilled in the art can flexibly set the structure and size of the body structural member according to an actual situation.

Figure 2:
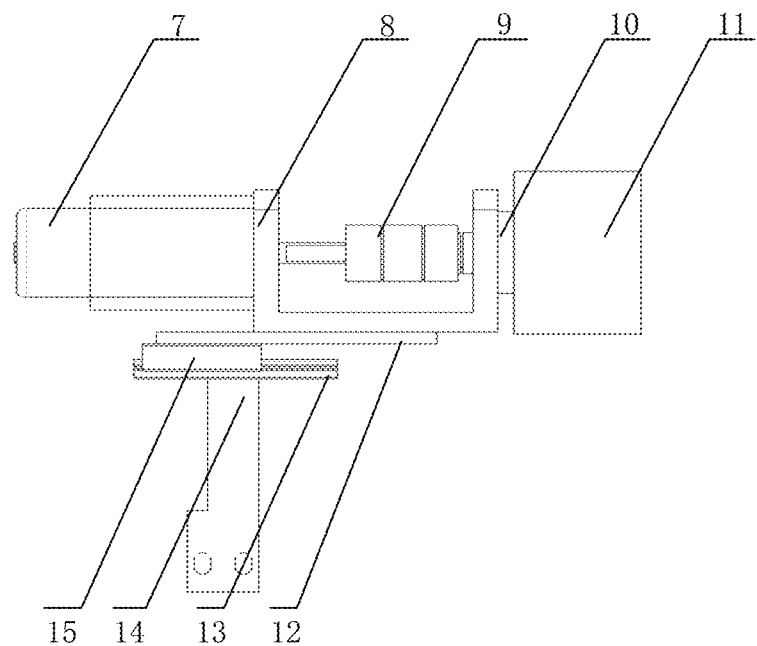
FIG. 2 is a schematic structural diagram of a main finger assembly in an embodiment of the present invention.

Further, referring to FIG. 2, the main finger assembly 1 includes a main finger power device, a main finger transmission mechanism, and a main finger guide rail mechanism, wherein the main finger transmission mechanism includes the coupling 9, the main finger power device includes the propelling motor 7, an output shaft of the propelling motor 7 is coaxially connected to the main roller 11 through the coupling 9, the propelling motor 7 is connected to the controller through a communication link, and the main roller 11 is driven by the propelling motor 7 to rotate axially about the output shaft of the propelling motor 7. The main finger guide rail mechanism includes the main finger guide rail 13 and the main finger slider 15, the main finger guide rail 13 is vertically fixed to the web plate 47, and the main roller 11 is slidingly disposed to the main finger guide rail 13 through the main finger slider 15, to form a linear moving pair. The driving assembly 4 drives the main roller 11 to move up and down in a vertical direction through the linear moving pair.

Specifically, the main finger assembly 1 includes the propelling motor 7, the main shaft connecting member 8, the coupling 9, the support shaft 10, the main roller 11, the connecting plate 12, the main finger guide rail 13, the nut connecting frame 14, and the main finger slider 15. Unlike the conventional device, the present invention can realize the delivery action of the two guide wires or catheters. The propelling motor 7 is fixed on the main shaft connecting member 8 by bolts, the output shaft of the propelling motor 7 is connected to the support shaft 10 through the coupling 9, the main roller 11 is coaxially connected to the support shaft 10, and the main shaft connecting member 8 supports and fixes the support shaft 10. A rubber jacket is provided on the surface of the main roller 11 to increase the friction between the guide wire or catheter and the roller. The main shaft connecting member 8 is bolted to the connecting plate 12. The connecting plate 12 is bolted to the main finger slider 15. The main finger slider 15 is connected to the main finger guide rail 13 through a guide rail pair. The connecting plate 12 is bolted to the nut connecting frame 14. The nut connecting frame 14 is bolted to the driving assembly 4.

The forward/reverse rotational motion of the main roller can realize the advancement or retreat of the guide wire or balloon with the following transmission relationship: the output shaft of the propelling motor 7 rotates to drive the support shaft 10 and the main roller 11 to rotate through the coupling 9, its advancement or retreat is realized through the friction between the main roller 11 and the guide wire or balloon, and the axial relative movement of the main finger assembly 1 and the first/second sub-finger assembly realizes the rotational motion of the guide wire or catheter to simulate an action of hand twisting. Since the rotation directions of the two sub-rollers are the same, and are each opposite to the rotation direction of the main roller 11, but their relative positional relationships with the main roller 11 are different, a friction force between the main roller 11 and the first sub-roller 29, and a friction force between the main roller 11 and the second sub-roller are different in direction. Therefore, the main roller is required to rotate in the opposite directions when the two guide wires are advanced. That is, when the first guide wire advances, the main roller needs to rotate clockwise, and when the second guide wire advances, the main roller needs to rotate counterclockwise. It should be noted that due to surgical needs, the two guide wires cannot be moved simultaneously.

Continuing to refer to FIG. 3, FIG. 3 is a schematic structural diagram of the first sub-finger assembly 2 of the present invention. Since the first sub-finger assembly and the second sub-finger assembly have substantially the same structure and motion relationship, the first sub-finger assembly is taken as an example for description. The first sub-finger assembly and the second sub-finger assembly each include a wheelbase adjustment device and a sub-finger guide rail mechanism, and the wheelbase adjustment device includes a sub-finger power device and a sub-finger transmission mechanism. The sub-finger transmission mechanism is a gear transmission, the sub-finger power device includes a clamping motor, and rotational motions of output shafts of the two clamping motors drive the first sub-roller and the second sub-roller to move toward or away from the main roller by means of gear transmission, respectively.

The sub-finger guide rail mechanism includes a sub-finger guide rail and a sub-finger slider. The two sub-finger guide rails are symmetrically arranged on both sides of the main finger guide rail, and are each vertically fixed to the web plate 47. The first sub-roller and the second sub-roller are slidingly disposed to the sub-finger guide rail through the sub-finger slider, respectively, to form a first linearly moving pair and a second linearly moving pair. The driving assembly drives the first sub-roller and the second sub-roller to move up and down in the vertical direction through the first linear moving pair and the second linear moving pair, respectively.

Specifically, in an embodiment of the present invention, the sub-finger transmission mechanism is provided as a combination of gears and guide rails for transmission. Those skilled in the art can freely change the structure of the transmission mechanism as long as the roller can be moved. The first sub-finger assembly of this embodiment includes the clamping motor 16, the clamping motor connecting member 17, the gear 18, the inclined pad 19, the connecting plate 20, the sub-finger slider 21, the sub-finger guide rail 22, the nut connecting bracket 23, the tooth block 24, the roller moving slider 25, the roller moving guide rail 26, the roller support frame 27, the first support shaft 28, and the first sub-roller 29.

The clamping motor 16 is fixed on the clamping motor connecting member 17. The clamping motor connecting member 17 is bolted to the inclined pad 19. The inclined pad 19 is bolted to the connecting plate 20, and the connecting plate 20 is bolted to the sub-finger slider 21. The sub-finger slider 21 is connected to the sub-finger guide rail 22 through a guide rail pair. The sub-finger guide rail 22 is fixedly connected to the web plate of the body structural member by bolts. The connecting plate 20 is bolted to the nut connecting bracket 23. The clamping motor 16 is connected to the controller through a communication link. An output shaft of the clamping motor 16 is directly connected to the gear 18. The gear 18 is meshed with the tooth block 24, and the tooth block 24 is bolted to the roller support frame 27. The roller support frame 27 is used to fix the first support shaft 28, and is fastened by bolts. The first support shaft 28 and the first sub-roller 29 are coaxially connected. In addition, the tooth block 24 is bolted to the roller moving slider 25, the roller moving slider 25 is connected to the roller moving guide rail 26 through a guide rail pair, and the roller moving guide rail 26 is bolted to the inclined pad 19. In order to increase the friction between the guide wire or catheter and the sub-roller, a rubber jacket is provided on the surface of the sub-roller.

The first sub-finger assembly mainly includes three motions. The first is the rotation of the first sub-roller. The main roller drives the guide wire or catheter to move, and the guide wire or catheter drives the first sub-roller to rotate, realizing the backward/forward movement of the guide wire. The second is the axial relative movement between the first sub-roller and the main roller. The third is the clamping motion of the first sub-roller. It is driven by the clamping motor, and the gear is meshed with the tooth block for transmission to drive the first sub-roller to move, realizing the adjustment of the distance between the main roller and the first sub-roller, which adapts to different specifications of guide wires or catheters.

The transmission relationships are as follows: the output shaft of the clamping motor 16 rotates to drive the gear 18 to rotate, the gear 18 is meshed with the tooth block 24 to convert the rotational motion into a linear translational motion, so that the tooth block 24 and the slider 25 move linearly along the guide rail 26 while simultaneously driving the roller support frame 27, and the first support shaft 28 and the first sub-roller 29 move linearly to adjust the distance between the main roller 11 and the first sub-roller 29. Due to the positional relationship between the two sub-rollers and the main roller, when the two guide wires advance forward, the rotation direction of the main roller 11 is required to be opposite.

Figure 4:
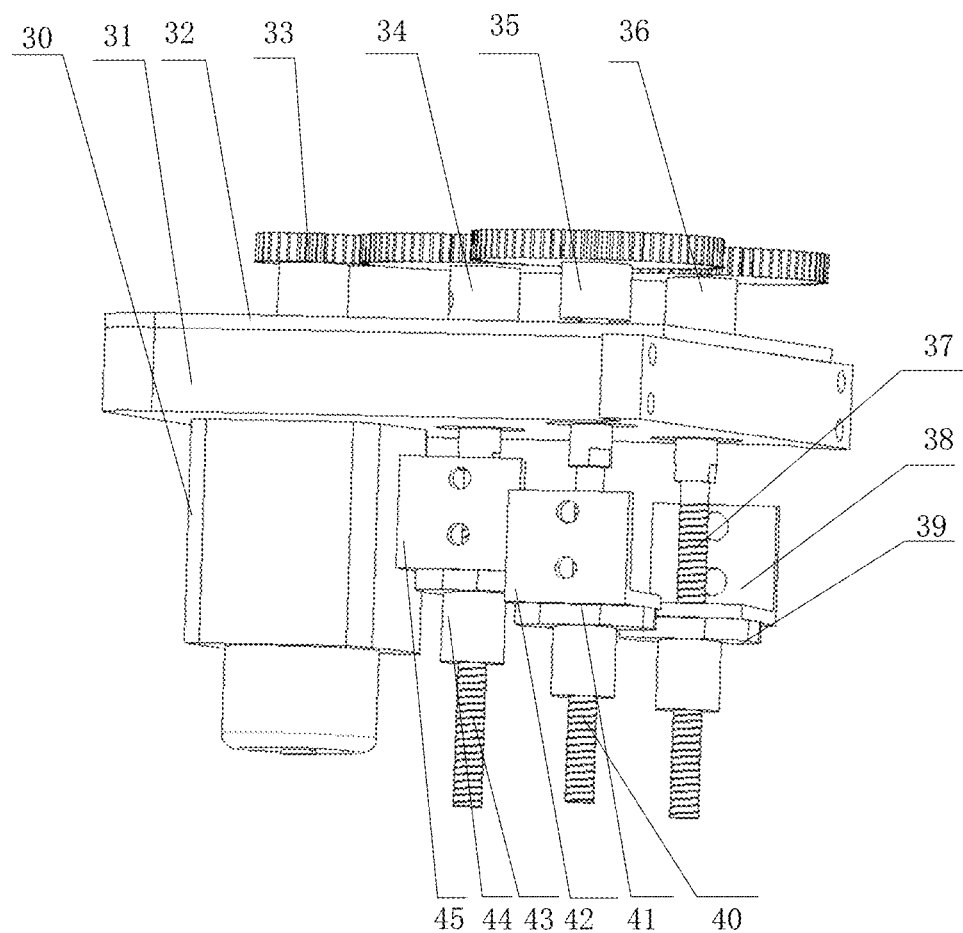
FIG. 4 is a schematic structural diagram of a driving assembly in an embodiment of the present invention.

The driving assembly of the present invention includes a first power device, a main finger assembly transmission member, a first sub-finger assembly transmission member, and a second sub-finger assembly transmission member. The main finger assembly transmission member is driven by the first power device to perform a repetitive displacement motion with the first sub-finger assembly transmission member and/or the second sub-finger assembly transmission member, so that the main finger assembly and the first sub-finger assembly and/or the second sub-finger assembly form an axial displacement to twist the clamped guide wire or balloon being operated to rotate. FIG. 4 is a schematic structural diagram of the driving assembly of the embodiment. In the embodiment, a thrust plate is preferably provided to fix and install the first power device and the transmission member for each assembly. In the embodiment, the main finger assembly transmission member, the first sub-finger assembly transmission member and the second sub-finger assembly transmission member are preferably provided as a combination of gear transmission and screw transmission. The main finger assembly transmission member, the first sub-finger assembly transmission member, and the second sub-finger assembly transmission member have the same structure, and each include a gear, a screw, and a screw base matched with the screw. The screw is disposed under the gear through the thrust plate and is coaxially connected with the gear. The screw base is sleeved on the screw. The three screw bases are connected to the main roller, the first sub-roller, and the second sub-roller, respectively. The first power device includes a twisting motor 30. The rotational motion of the output shaft of the twisting motor 30 is converted into a repetitive displacement motion through the transmission of the gear and the screw.

Specifically, in order to facilitate observation and understanding, the driving assembly of this embodiment is reversed in FIG. 4 with respect to the direction shown in FIG. 1. FIG. 4 is a schematic structural diagram of an embodiment of the driving assembly of the present invention. The driving assembly of this embodiment includes the twisting motor 30, the bearing support unit 31, the bearing thrust plate 32, the main gear 33, the slave gear 34, the slave gear 35, the slave gear 36, the screw 37, the nut connecting frame 38, the screw base 39, the screw 40, the screw base 41, the nut connecting frame 42, the screw 43, the screw base 44, and the nut connecting frame 45. The above-mentioned thrust plate is the bearing thrust plate 32. The slave gear 34, the screw 43 and the screw base 44 sleeved on the screw 43 together form the main finger assembly transmission. Similarly, the slave gear 35, the screw 40 and the screw base 41 sleeved on the screw 40 together form the second sub-finger assembly transmission member; and the gear 36, the screw 37 and the screw base 39 sleeved on the screw 37 together form the first sub-finger assembly transmission member.

Further, the twisting motor 30 is connected to the controller through a communication link. The twisting motor 30 is bolted to the bearing support unit 31 and the bearing thrust plate 32. The output shaft of the twisting motor 30 is fixed to the main gear 33, the main gear 33 is meshed with the slave gear 34, and the slave gear 34 is meshed with the slave gear 35 and the slave gear 36 at the same time. The three slave gears are connected with the corresponding screws, respectively. The screw 37, the screw 40 and the screw 43 are fixedly supported by the bearing support unit 31, and are bolted to the nut connecting frame 38, the nut connecting frame 42 and the nut connecting frame 45, respectively. It should be noted that the screw 37, the screw 40 and the screw 4 have the same screw pitch specifications. The bearing thrust plate 32 has two functions, one of which is to install a twisting motor as a motor frame, and the other of which is to be used for screw bearing thrust to contact the bearing support unit 31. The rotation direction of the slave gear 34 is opposite to that of the slave gear 35 and the gear 36, and the corresponding linear movement direction of the screw 43 is opposite to that of the screw 37 and the screw 40, which can realize the twisting motion of the guide wire.

The twisting motor provides power for the twisting motion, the gears are meshed to transmit motion and force, the rotational motion is converted into a linear motion by means of screw transmission, and the guide rail pairs are used in cooperation to transmit the motion to the main finger assembly 1, the first sub-finger assembly 2 and the second sub-finger assembly 3, realizing the linear movement along the axial direction of the guide rail. The specific transmission relationships are as follows: the output shaft of the twisting motor 30 drives the main gear 33 to rotate, the main gear 33 is meshed with the slave gear 34, the slave gear 34 is meshed with the slave gear 35 and the slave gear 36 at the same time, and the slave gear 35 and the slave gear 36 are not in contact; and then the motion is transferred to the main finger assembly 1, the first sub-finger assembly 2 and the second sub-finger assembly 3 through the screw bases and the nut connecting frames. It should be noted that this structure is only an illustration of this embodiment, and the present invention can also use a combination of bevel gears and racks to realize the conversion of the rotational motion of the twisting motor 30 into a linear motion. The power device of the driving assembly of the present invention can also use other driving manners to replace the motor. Those skilled in the art can also flexibly set the structures of the assembly transmission members and the structure of the power device according to actual applications. They will not be exhaustively listed here. Changes in the structure of the drive assembly each do not exceed the principles and concepts of the present invention, and each should be limited to the protection scope of the present invention.

In the clamping assembly of the present invention, the first clamping assembly and the second clamping assembly have the same structure, and each include a second power device and a clamping transmission assembly. The clamping transmission assembly includes a fixed part and a movable part. The movable part is driven by the second power device to perform a repetitive displacement motion, so that the fixed part and the movable part form a moving pair for clamping or releasing the operated guide wire or balloon. During surgery, the two guide wires or balloons can not completely realize the positioning and guidance of the guide wires or balloons only by the clamping of the main roller and the sub-roller. When it is not properly operated, the guide wires or balloons are likely to deviate from a target direction. In the present invention, the clamping assembly is disposed to clamp the guide wire or balloon. On the one hand, it can assist the main roller and the sub-roller to clamp the guide wire or balloon, avoiding the yaw of the guide wire or balloon. On the other hand, when one guide wires/balloon of the two guide wires or balloons is operated, the clamping assembly can clamp and fix the other guide wire or balloon that is not operated, avoiding its wandering away from the lesion or interference with the operated guide wire or balloon. In an actual surgery, when a doctor is operating one guide wire or balloon, the action of fixing the other guide wire or balloon is held by the doctor's hand for a long time, which has large labor intensity, is easy to cause arm numbness, and is not easy to control, resulting in poor surgical safety. The design of the clamping assembly of the present invention, on the one hand, reduces the doctor's operation burden, and on the other hand, ensures that the surgery is efficiently carried out.

Specifically, the fixed part includes a clamping guide rail and a fixed clamping end. The movable part includes a clamping slider that cooperates with the clamping guide rail, and a movable clamping end. The clamping slider is connected to the movable clamping end, the fixed clamping end and the movable clamping end are disposed symmetrically, and the fixed clamping end and the movable clamping end are each provided with a guide groove at an end close to each other. The second power device includes a clamping motor, a clamping gear is provided on an output shaft of the clamping motor, the clamping slider is provided with a rack meshed with the clamping gear at an end close to the clamping gear, and the second power device drives the clamping gear so that the slider drives the movable clamping end to displace.

Figure 6:
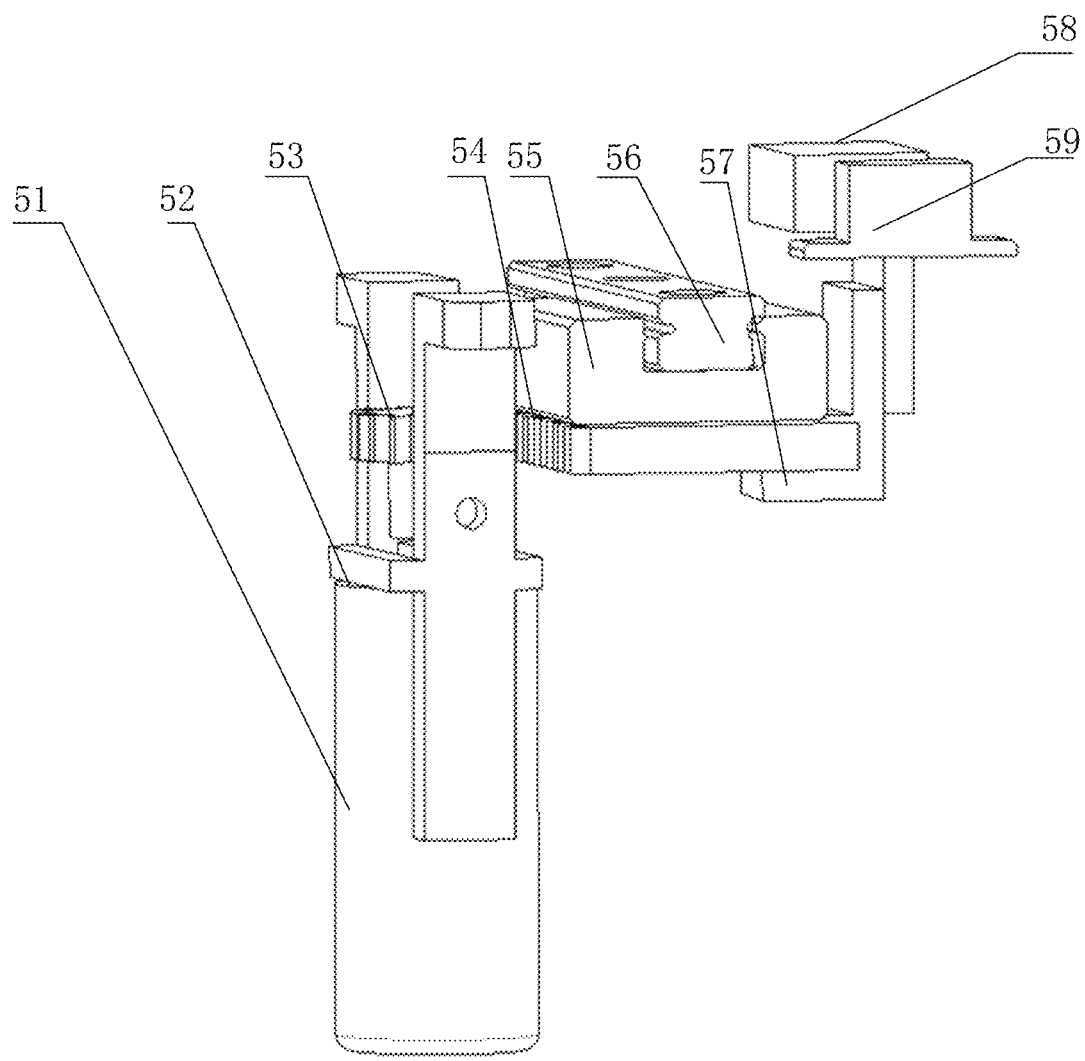
FIG. 6 is a schematic structural diagram of a clamping assembly in an embodiment of the present invention.

FIG. 6 is a structural diagram of the clamping assembly 6. Referring to FIG. 6, the clamping assembly of the present invention includes two parts, which realize the clamping of two guide wires, respectively. The two clamping assemblies have the same structure and function. Therefore, the first clamping assembly is used as an example for illustration. The clamping assembly corresponds to the guide wire or balloon in the first sub-finger assembly. It should be noted that the two clamping assemblies are separately installed to the top plate 46 to avoid interference with each other. The first clamping assembly includes a second power device and a clamping transmission assembly. The second power device includes the clamping motor 51. The clamping transmission assembly includes a fixed part and a movable part. The fixed part includes the clamping guide rail 56 and the fixed clamping end 59. The movable part includes the clamping slider 55 cooperating with the clamping guide rail, and the movable clamping end 58. In addition, this embodiment also includes the tooth block 54, the clamping motor connecting member 52, the clamping gear 53, the tooth block 54, and the connecting lever 57.

The clamping motor 51 is connected to the controller through a communication link. The clamping motor 51 is bolted and fixed to the top plate 46 through the clamping motor connecting member 52. The output shaft of the clamping motor 51 is directly connected to the clamping gear 53. The clamping gear 53 is meshed with the tooth block 54, and the tooth block 54 is bolted to the clamping slider 55. The clamping slider 55 is connected to the clamping guide rail 56 through a guide rail pair. The connecting lever 57 is bolted to the clamping slider 55. The movable clamping end 58 is bolted to the connecting lever 57. The fixed clamping end 59 is vertically installed along a centerline direction of the clamping guide rail 56 and is connected onto the top plate 46 by bolts. The movable clamping end 58 and the fixed clamping end 59 are provided with guide grooves for the guide wire to pass therethrough, which are mainly used for clamping the guide wire or the catheter. The two clamping assemblies are preferably distributed symmetrically, and their installation directions are perpendicular to the tangential directions of the main roller and the sub-roller, so that the guide wire or catheter can be advanced along the tangential directions. Those skilled in the art can also flexibly adjust the installation position of the clamping assembly according to an actual situation, as long as it can ensure that the clamped guide wire or balloon can pass through the tangential directions of the main roller and the sub-roller and will not affect the damage of the guide wire or balloon. The specific installation manner of the clamping assembly can also be set with reference to the single guide wire control device in the prior art.

The transmission relationship of the clamping assembly is as follows: the clamping motor 51 rotates to drive the clamping gear 53 to move, the clamping gear 53 is meshed with the tooth block 54 and drives the clamping slider 55 to move along the clamping guide rail 56, and the connecting lever 57 is bolted to the movable clamping end 58 to adjust the distance between the movable clamping end 58 and the fixed clamping end 59 so as to adapt to guide wires or catheters or balloons of different specifications.

It should be noted that the transmission manner of the above-mentioned clamping assembly is only an example, and those skilled in the art can also flexibly set the second power device according to actual needs. For example, the motor is replaced by a manner of hydraulic drive, pneumatic tendon, electric drive, or the like. The clamping transmission assembly can also be flexibly set according to needs. For example, the clamping gear 53 and the tooth block 54 are integrally formed. The schematic structure of this embodiment may also be replaced by a transmission manner such as a gear rack, and a ball screw, as long as the clamping assembly can realize the clamping or release of the guide wire or balloon. They will not be exhaustively listed here. Such an adjustment of the structure of the clamping assembly does not deviate from the principle and scope of the present invention, and should be defined within the protection scope of the present invention.

The technical solutions in the embodiments of the present application described above have at least the following technical effects and advantages.

In the present invention, the two sub-rollers approximate to and separate from the main roller by the wheelbase adjusting devices in the two sub-finger assemblies, respectively, to clamp or release the two guide wires or balloons, and the relative movement between the main roller and the sub-rollers advances and rotates the clamped guide wire or balloon, thereby realizing separate control of the two guide. The two guide wires or balloons are separately powered by the propelling motor in the main finger assembly to realize the forward/backward movement. The relative movement of each guide wire or balloon along the axial direction is powered by the twisting motor in the driving assembly to realize the combined movement between the main roller and the sub-rollers, thereby realizing the forward and reverse rotation motions of the guide wire or balloon catheter. It is powered by the clamping motor in the sub-finger assembly to realize the distance adjustment and tensioning work between the main roller and the sub-rollers. After the guide wire or balloon reaches the lesion location, the guide wire or balloon is clamped by the clamping assembly to prevent the guide wire or balloon from wandering. The operation of pushing the double guide wires is realized through the above actions, which can save the operation step of the doctor to replace the surgical instrument, reduce the doctor's operation burden, improve the surgical efficiency, reduce the surgical cost, reduce the patient's pain, enhance the patient's comfort during surgery, and ensure that the surgery is carried out smoothly, which has strong clinical applicability and wide application prospects.

It should be noted that in the description of the present invention, "guide wire" can be replaced with "catheter", "guide wire or balloon" can be replaced with "guide wire or balloon" or "combination connecting structure of guide wire and balloon". The vascular interventional instrument control device with double guide wires or balloons of the present invention can control double guide wires or double balloons or double catheters, which may be replaced by medical tools as long as they conform to the installation dimensions of the present invention and the driving principles of the present invention. They will not be exhaustively listed here. It should be noted that the terms in the description of the present application document and the title of the present invention are only for the convenience of description, and do not indicate or imply the limitation of the application of the present invention. The title of the present invention is not intended to limit the use of the present invention.

The terms "center", "upper", "lower", "left", "right", "vertical", "horizontal", "inner", "outer" and other terms indicating directions or positional relationships are based on the directions or positional relationships shown in the drawings, which is only for convenience of description, and does not indicate or imply that the device or element must have a specific orientation, be constructed and operated in a specific orientation. Therefore, they cannot be construed as limiting the present invention. In addition, the terms "first", "second", and "third" are for descriptive purposes only, and cannot be understood as indicating or implying relative importance.

In addition, it should also be noted that, in the description of the present invention, unless otherwise clearly specified and defined, the terms "installed", "connected" and "connecting" should be broadly understood. For example, it may be a fixed connection, or may be a detachable connection or an integral connection; it may be a mechanical connection, or may be an electrical connection; and it can be a direct connection, or may be an indirectly connection by means of an intermediate medium, or may be a communication between two elements. For those skilled in the art, the specific meanings of the above terms in the present invention can be understood according to specific situations.

The term "comprise/include" or any other similar language is intended to cover non-exclusive inclusions, so that a process, article or apparatus/device that includes a series of elements includes not only those elements, but also includes other elements not explicitly listed, or also includes elements inherent to the process, article, or apparatus/device.

So far, the technical solutions of the present invention have been described in conjunction with the preferred embodiments shown in the drawings. However, it is easily understood by those skilled in the art that the protection scope of the present invention is obviously not limited to these specific embodiments. Without departing from the principle of the present invention, those skilled in the art can make equivalent changes or replacements to related technical features, and the technical solutions after these changes or replacements will fall within the protection scope of the present invention.

What is claimed is:

1. A vascular interventional instrument control device with double guide wires or balloons, comprising a body structural member, a main finger assembly, a sub-finger assembly, a driving assembly, a clamping assembly and a controller, wherein the main finger assembly, the sub-finger assembly, the driving assembly and the clamping assembly are separately installed to the body structural member and separately connected to the controller through a communication link, the sub-finger assembly comprises a first sub-finger assembly and a second sub-finger assembly, and the clamping assembly comprises a first clamping assembly for clamping a first guide wire or balloon, and a second clamping assembly for clamping a second guide wire or balloon;

the main finger assembly comprises a main roller, the first sub-finger assembly comprises a first sub-roller, and the second sub-finger assembly comprises a second sub-roller; the main roller, the first sub-roller, and the second sub-roller have axes disposed in parallel; and the first sub-roller and the second sub-roller are mirror-symmetrical with respect to an axis of the main roller;

the first sub-finger assembly is provided with a first wheelbase adjustment device, an axial distance between the first sub-roller and the main roller is adjusted by the first wheelbase adjustment device to clamp or release the first guide wire or balloon; and the second sub-finger assembly is provided with a second wheelbase adjustment device, an axial distance between the second sub-roller and the main roller is adjusted by the second wheelbase adjustment device-to clamp or release the second guide wire or balloon;

when the first guide wire or balloon is clamped by the main roller and the first sub-roller, the first guide wire or balloon is displaced along an axial direction of the first guide wire or balloon by axial rotation of the main roller; the main finger assembly, and the first sub-finger assembly is separately moved axially by driving of the driving assembly, for twisting the first guide wire or balloon to rotate about the axial direction of the first guide wire or balloon; and when the second guide wire or balloon is clamped by the main roller and the second sub-roller, the second guide wire or balloon is displaced along an axial direction of the second guide wire or balloon by axial rotation of the main roller; the main finger assembly, and the second sub-finger assembly is separately moved axially by the driving of the driving assembly, for twisting the second guide wire or balloon to rotate about the axial direction of the second guide wire or balloon.

2. The vascular interventional instrument control device according to claim 1, wherein the first sub-roller is driven close to or away from the main roller by the first wheelbase adjustment device, and the first guide wire or balloon disposed between the first sub-roller and the main roller is clamped or released;

the second sub-roller is driven close to or away from the main roller by the second wheelbase adjustment device, and the second guide wire or balloon disposed between the second sub-roller and the main roller is clamped or released; and at the same time, the first guide wire or balloon and the second guide wire or balloon are operated in different clamping states, and movement of the main roller does not interfere with the first guide wire or balloon and the second guide wire or balloon after each is respectively released.

3. The vascular interventional instrument control device according to claim 1, wherein the body structural member comprises a top plate and a web plate perpendicular to the top plate, and at least three through holes are provided on the web plate; and the body structural member is divided into a driving part and an executing part by the web plate, the main finger assembly, the first sub-finger assembly, and the second sub-finger assembly are separately disposed in the executing part, and the driving assembly and the clamping assembly are disposed in the driving part.

4. The vascular interventional instrument control device according to claim 3, wherein the main finger assembly comprises a main finger power device, a main finger transmission mechanism and a main finger guide rail mechanism, the main finger transmission mechanism comprises a coupling, the main finger power device comprises a propelling motor, an output shaft of the propelling motor is coaxially connected to the main roller through the coupling, and the main roller is driven by the propelling motor to rotate axially about the output shaft of the propelling motor;

the main finger guide rail mechanism comprises a main finger guide rail and a main finger slider, the main finger guide rail is vertically fixed to the web plate, and the main roller is slidingly disposed to the main finger guide rail through the main finger slider to form a linearly moving pair; and the main roller is driven by the driving assembly to move up and down along a vertical direction through the linearly moving pair.

5. The vascular interventional instrument control device according to claim 3, wherein the first sub-finger assembly and the second sub-finger assembly have the same structure, and the first sub-finger assembly comprises the first wheelbase adjustment device and a first sub-finger guide rail mechanism, and the second sub-finger assembly comprises the second wheelbase adjustment device and a second sub-finger guide rail mechanism wherein the first wheelbase adjustment device comprises a first sub-finger power device and a first sub-finger transmission mechanism, the second wheelbase adjustment device comprises a second sub-finger power device and a second sub-finger transmission mechanism; and the first sub-finger transmission mechanism and the second sub-finger transmission mechanism are gear transmissions, the first sub-finger power device comprises a first clamping motor, and the second sub-finger power device comprises a second clamping motor, and rotational motions of output shafts of the first clamping motor and the second clamping motor drive the first sub-roller and the second sub-roller to move toward or away from the main roller by the gear transmissions, respectively;

the first sub-finger guide rail mechanism comprises a first sub-finger guide rail and a first sub-finger slider, the second sub-finger guide rail mechanism comprises a second sub-finger guide rail and a second sub-finger slider, the first sub-finger guide rail and the second sub-finger guide rail are symmetrically arranged on both sides of the main finger guide rail, and both are fixed vertically to the web plate, the first sub-roller is slidingly disposed to the first sub-finger guide rail through the first sub-finger slider, to form a first linearly moving pair, the second sub-roller is slidingly disposed to the second sub-finger guide rail through the second sub-finger slider, to form a second linearly moving pair; and the driving assembly drives the first sub-roller and the second sub-roller to move up and down along a vertical direction through the first linearly moving pair and the second linearly moving pair, respectively.

6. The vascular interventional instrument control device according to claim 3, wherein the driving assembly comprises a first power device, a main finger assembly transmission member, a first sub-finger assembly transmission member, and a second sub-finger assembly transmission member; the main finger assembly transmission member is driven by the first power device to perform a repetitive displacement motion with the first sub-finger assembly transmission member and/or the second sub-finger assembly transmission member, so that the main finger assembly and the first sub-finger assembly form an axial displacement to twist the first guide wire or balloon being operated to rotate, and the main finger assembly and the second sub-finger assembly form an axial displacement to twist the second guide wire or balloon being operated to rotate.

7. The vascular interventional instrument control device according to claim 6, wherein the driving assembly further comprises a thrust plate, the main finger assembly transmission member, the first sub-finger assembly transmission member and the second sub-finger assembly transmission member have the same structure, and each of the main finger assembly transmission member, the first sub-finger assembly transmission member and the second sub-finger assembly transmission member comprises a gear, a screw, and a screw base matched with the screw, the screw is disposed below the gear through the thrust plate and is coaxially connected to the gear, the screw base is sleeved to the screw, and the screw bases of the main finger assembly transmission member, the first sub-finger assembly transmission member and the second sub-finger assembly transmission member are connected to the main roller assembly, the first sub-roller assembly, and the second sub-roller assembly, respectively; and the first power device comprising a twisting motor; a rotational motion of an output shaft of the twisting motor is converted into a repetitive displacement motion through the gear and the screw and is transferred to the main roller assembly, the first sub-roller assembly and the second sub-roller assembly.

8. The vascular interventional instrument control device according to claim 3, wherein the first clamping assembly and the second clamping assembly have the same structure, and each of the first clamping assembly and the second clamping assembly comprises a second power device, and a clamping transmission assembly, and the clamping transmission assembly comprises a fixed part and a movable part, and the movable part is driven by the second power device to perform the repetitive displacement motion, and the fixed part and the movable part form a moving pair for clamping or releasing the first guide wire or balloon and the second guide wire or balloon.

9. The vascular interventional instrument control device according to claim 8, wherein the fixed part comprises a clamping guide rail and a fixed clamping end, the movable part comprises a clamping slider and a movable clamping end, the clamping slider cooperates with the clamping guide rail, the clamping slider is connected to the movable clamping end, the fixed clamping end is symmetrically disposed with the movable clamping end, and the fixed clamping end and the movable clamping end are each provided with a guide groove at an end close to each other; and the second power device comprises a clamping motor, a clamping gear is provided on an output shaft of the clamping motor, the clamping slider is provided with a rack meshed with the clamping gear at an end close to the clamping gear, and the second power device drives the clamping gear, and the clamping slider drives the movable clamping end to displace.

10. The vascular interventional instrument control device according to claim 1, wherein the main roller, the first sub-roller, and the second sub-roller each comprise a roller and a rubber jacket, and the rubber jacket is sleeved on the roller through an interference fit.

* * * * *